United States Patent [19]
Mayes

[11] Patent Number: 5,861,526
[45] Date of Patent: Jan. 19, 1999

[54] PROCESS FOR REDUCING DITHIOCARBAZINATE BUILDUP IN THE PREPARATION OF METHYL DITHIOCARBAZINATE

[75] Inventor: David M. Mayes, Overland Park, Kans.

[73] Assignee: Bayer Corporation, Pittsburgh, Pa.

[21] Appl. No.: 869,325

[22] Filed: Jun. 5, 1997

Related U.S. Application Data

[63] Continuation-in-part of Ser. No. 743,775, Nov. 7, 1996, abandoned.

[51] Int. Cl.$^6$ .................................................. C07C 333/00
[52] U.S. Cl. ................................................ 558/233
[58] Field of Search ............................................... 558/233

[56] References Cited

U.S. PATENT DOCUMENTS

| | | | |
|---|---|---|---|
| 3,284,482 | 11/1966 | D'Amico et al. | 260/455 |
| 4,696,938 | 9/1987 | Le | 514/343 |

FOREIGN PATENT DOCUMENTS

| | | |
|---|---|---|
| 3709414 | 2/1988 | Germany . |
| 1274521 | 5/1972 | United Kingdom . |

OTHER PUBLICATIONS

Audrieth et al., J. Organic Chem., vol. 19, pp. 733–741(month unavailable) 1954.
S. Losanitch, J. Chem. Soc., vol. 119, pp.763–765 (month unavailable) 1921.
Sandström et al, Arkiv För Kemi, 4 (month unavailable) 1952 p. 297.

*Primary Examiner*—Peter O'Sullivan
*Attorney, Agent, or Firm*—Joseph C. Gil

[57] ABSTRACT

Disclosed herein is an improved process for preparing methyl dithiocarbazinate by reacting carbon disulfide and hydrazine in an effective ratio to form hydrazinium dithiocarbazinate, followed by methylating the hydrazinium dithiocarbazinate with methyl bromide. The improvement resides in conducting the reaction of the carbon disulfide and hydrazine in the presence of a specified amount of a non-alcoholic solvent to reduce dithiocarbazinate buildup.

6 Claims, No Drawings

PROCESS FOR REDUCING DITHIOCARBAZINATE BUILDUP IN THE PREPARATION OF METHYL DITHIOCARBAZINATE

CROSS REFERENCE TO RELATED APPLICATION

This application is a continuation-in-part of U.S. application Ser. No. 08/743,775, filed on Nov. 7, 1996, now abandoned.

BACKGROUND OF THE INVENTION

1. Field of the Invention

The present invention relates to an improved process for preparing methyl dithiocarbazinate. More specifically, the invention relates to an improved process for improving the yield and/or purity of methyl dithiocarbazinate.

2. Brief Description of the Prior Art

The prior art disclosures of the processes for preparing methyl dithiocarbazinate are limited by the paucity of information on reported experimental procedures and the excessive cost of commercial scale procedures. Laboratory reports present little information on how reaction temperatures would affect production of undesirable by-products, yield and purity, impact on waste treatment operations and the like. Commercial scale procedures are expensive because they involve the use of expensive reagents and/or expensive techniques such as separation of intermediate products and recrystallization of the final product.

Audrieth et al., J. Organic Chem., Vol. 19, pp. 733–741 (1954) discloses a process for preparing methyl dithiocarbazinate and converting it to thiocarbohydrazide. The process comprises a dropwise addition of 1.04 moles of carbon disulfide to 1.18 moles of potassium hydroxide and 1.1 moles of 85% hydrazine in 200 ml. of ethanol, in an ice bath. A heavy yellow oil containing potassium dithiocarbazinate separates during the addition. The resulting mixture is stirred and chilled and two volumes of ether are added to cause separation of more of the desired product (potassium dithiocarbazinate).

The oily layer is separated from the ether-alcohol layer and filtered to remove a small amount of an unidentified solid that is formed. The clear yellow solution is then dissolved in 300 ml. of water. The resulting solution is cooled in an ice bath and 1.05 moles of methyl iodide are added in approximately 10 batches. The reaction vessel is shaken and cooled alternately after each such addition until the methyl iodide is consumed. The reaction mixture is allowed to stand for several hours, being shaken occasionally to permit complete reaction. The methyl dithiocarbazinate is collected and recrystallized from ethanol.

Methyl dithiocarbazinate (24.4 gm., 0.2 mole) was dissolved in 200 ml. of absolute ethanol and 18 ml. (0.3 mole of hydrazine) of 85% hydrazine hydrate was added. The resulting solution was refluxed until no more solid thiocarbohydrazide precipitated (about 45 minutes). A small amount of 3-hydrazino-4-amino-5-mercapto-1,2,4-triazole that had formed was removed as follows. The reaction mixture was chilled, and the resulting solid product was collected and recrystallized from water acidified with a few drops of hydrochloric acid.

U.S. Pat. No. 4,696,938 discloses a process for preparing and using methyl hydrazinecarbodithioate as an intermediate in the preparation of 6-aryl-pyridine thiosemicarbazones. Methyl dithio-carbazinate is prepared as follows. Hydrazine hydrate (150 g) is added to a cooled (0° C.) solution of potassium hydroxide in water (240 ml.) and 2-propanol (200 ml.). Pre-cooled carbon disulfide (182 ml.) is then added dropwise to the stirred reaction mixture, while maintaining an internal temperature below 10° C. After the addition is complete, stirring is continued for a further one hour. Cooled methyl iodide (426 g) is added dropwise over 1½ hours. The resulting white precipitate is collected by filtration and washed with cooled water. The crude product is recrystalized from methylene chloride.

To form 6-aryl-pyridine thiosemicarbazone, methyl dithiocarbazinate is reacted in a suitable solvent such as alcohol. The reaction product is treated with selenium dioxide in a suitable ethereal solvent such as tetrahydrofuran or 1,4-dioxane.

S. Losanitch, J. Chem. Soc., Vol. 119, pp. 763–765 (1921) discloses a process for preparing methyl dithiocarbazinate by first obtaining ammonium dithiocarbazinate and reacting it with methyl iodide. The ammonium dithiocarbazinate is obtained as follows. A solution of hydrazine hydrate in alcohol, containing a large excess of ammonia, is slowly treated with cooling with the corresponding quantity of carbon disulfide. The methyl dithiocarbazinate is formed by treating the ammonium salt in a dilute alcohol solution with methyl iodide.

Sandström et al, Arkiv För Kemi, 4(1952) 297, discloses a process for preparing ethyldithiocarbazinate. The process involves the separation of hydrazinium dithiocarbazinate from an ethanol-water mixture and the reaction of the hydrazinium dithiocarbazinate with ethyl bromide in an ethanol-water mixture.

U.S. Pat. No. 3,284,482 discloses a process for preparing chlorobenzyl esters of dithiocarbazinic acid as follows. To a solution comprising 85% hydrazine, 25% sodium hydroxide and 300 ml. of water is added carbon disulfide, dropwise at 10° to 15° C. over 20 minutes. External cooling is removed and the reaction mixture is stirred for an hour at 25° to 30° C. Then, trichlorobenzyl chloride is added in one portion to the reaction mixture which is stirred for 24 hours at 25° to 30° C. to produce the corresponding trichlorobenzyl dithiocarbazinate. The product is then extracted with ethyl ether. The ether solution is washed with water until it becomes neutral, is dried over sodium sulfate, and the ether is removed in vacuo.

British Patent Specification 1,274,521 discloses dithiocarbazinic ester derivatives by reacting dithiocarbazinic acid esters with an oxo compound. The dithiocarbazinic acid is prepared by reacting hydrazine hydrate with carbon disulfide in alcohol medium in the presence of potassium hydroxide, ammonia or excess hydrazine hydrate.

After isolation, the dithiocarbazinic acid salt is converted into an ester by an alkylating or aralkylating step. This step is carried out in water, a mixture of water and alcohol or in alcohol. Alternately, the ester can be prepared in a single reactor. The alkylating or aralkylating agent is added to the dithiocarbazinic acid salt solution prepared by the above method. The alkylating or aralkylating agents disclosed by the patent are: dimethyl sulfate, diethyl sulfate, allyl chloride, n-butyl iodide, n-octyl ester, n-dodecyl bromide, cetyl bromide, benzyl chloride, p-chlorobenzyl chloride, p-isopropylbenzyl bromide, p-n-butylbenzyl bromide, and alpha-methylbenzyl chloride.

As would be realized from the foregoing, there is a need for an economic process, i.e., a more facile and cost efficient process for preparing methyl dithiocarbazinate. By the present invention, there is provided such an improved process for preparing methyl dithiocarbazinate.

SUMMARY OF THE INVENTION

In accordance with the foregoing, the present invention encompasses an improved process for preparing methyl dithiocarbazinate by reacting carbon disulfide and hydrazine to form hydrazinium dithiocarbazinate, followed by methylating the dithiocarbazinate with methyl bromide. The improvement comprises conducting the reaction of the carbon disulfide and the hydrazine in the presence of a non-alcoholic solvent to reduce dithiocarbazinate buildup on a surface to which it is exposed. The molar ratio of solvent to carbon disulfide is from about 0.4:1 to about 3:1, and is preferably from about 0.5:1 to about 3:1. Water is also preferably added.

The amount of solvent significantly exceeds the amount that is ordinarily employed in the prior art preparation of the hydrazinium dithiocarbazinate. Typically, the molar ratio of solvent to carbon disulfide in the prior art processes was 0.3:1 or less. It is relatively easy to ascertain reduction of surface buildup of dithiocarbazinate, typically, on the walls of reaction vessels, containers, conduits, or an apparatus therein. It has been found that about a two fold increase in the amount of solvent that is ordinarily employed can provide reduction in buildup. Amounts of solvent in excess of what is required to reduce buildup can adversely affect recovery of the reaction product or result in undue solvent stripping. This buildup is most clearly seen in pilot scale or industrial scale equipment but can be observed in laboratory scale equipment whose agitation style and intensity closely match industrial scale equipment. The use of increased solvent also provides the ability to produce a far more concentrated product slurry than is possible with water only or with water and lower levels of solvent. In the prior art, MDTC slurries with 25% or lower concentration were all that could be handled and transferred on an industrial scale. With the use of increased levels of solvent, slurries of 30 to 40% MDTC can be handled and transferred on an industrial scale. This provides a dramatic increase in the volumetric efficiency of production equipment with the corresponding reduction in product costs and waste generation.

By this process, one can unexpectedly obtain products of high purity (up to about 98%) and high yields (up to about 87%) with a 30 to 40% slurry concentration. In contrast, the prior art could not ordinarily attain product purity higher than 90 to 92% without further purification, and yields that were at 83% or higher and MDTC slurry concentration of 25% or lower were required for industrial use. Without being bound by any particular theory of the invention, it is believed that this process effects suspension of the solid product in a form that is easily mixed and transported. Apparently, the prior art process is unable to effect easy suspension and transportation of the solid product without excessive dilution. The invention is described more fully hereunder.

DETAILED DESCRIPTION OF THE INVENTION

As afore-stated, the claimed invention relates to an improved process for preparing methyl dithiocarbazinate by reacting carbon disulfide with hydrazine in a non-alcoholic solvent to form hydrazinium dithiocarbazinate. This is followed by methylating the hydrazinium dithiocarbazinate with methyl bromide to form methyl dithiocarbazinate. The improvement here comprises reducing buildup of dithiocarbazinate on the surface of the vessel by providing an increased level of solvent to reduce the buildup. The increased level of solvent can be added prior to or after the addition of carbon disulfide.

In the embodiment of the invention, referred to as the "HDTC process", the invention comprises reacting carbon disulfide with hydrazine in an effective ratio to form a reaction product containing hyradrazinium dithiocarbazinate. The resulting product comprising dithiocarbazinate is reacted with methyl bromide to produce high yields of methyl dithiocarbazinate.

In preparing the hydrazinium dithiocarbazinate by the HDTC process, hydrazine typically in the form of hydrazine hydrate, and carbon disulfide can be reacted in a mole ratio of from about 4:1 to about 2:1 and preferably from about 2:1 to about 2.4:1. The HDTC process can be represented by the following reaction scheme.

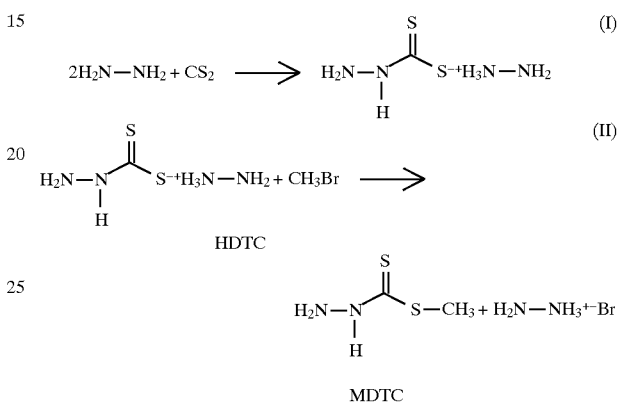

It is a distinct feature of the invention that one can harness the reaction medium to provide an improved process for preparing methyl dithiocarbazinate. As the reaction medium, one can employ a buildup reducing amount of a nonaqueous solvent. Preferably, the reaction mixture also contains water. When used, the molar ratio of water to carbon disulfide is from about 2:1 to about 10:1 and is preferably from about 2:1 to about 5:1. Useful non-alcoholic solvents are aprotic solvents. Illustratively, one can employ an aliphatic or aromatic hydrocarbon solvent. The aliphatic hydrocarbon can be selected from the group consisting of alkanes such as pentane, hexane, and heptane. The aromatic hydrocarbon can be selected from the group consisting of toluene, benzene and xylenes. Toluene is preferred. The molar ratio of solvent to carbon disulfide ranges from about 0.4:1 to about 3:1 and preferably from about 0.5:1 to about 3:1. Unlike many prior art processes, the reaction mixture (which may contain water) does not contain alcoholic solvents.

The above reactions can be conducted at a temperature of about 0° to 35° C. and preferably 5° to 25° C. over a period of about 1 to 4 hours and preferably 1 to 2 hours, at a pH of about 8 to 14 and preferably 9 to 14.

The resulting dithiocarbazinate is reacted (methylated) with methyl bromide. The mole ratio of methyl bromide to dithiocarbazinate can be from about 1.5 to 1.02:1, and preferably 1.05:1. Typically, methyl bromide is introduced into the reaction vessel containing the hydrazanium dithiocarbazinate by bubbling it through. While this reaction can be conducted in another reaction vessel, it is typically conducted in the same reaction vessel as used in preparing the dithiocarbazinate. The reaction medium employed in the methylation reaction is essentially the same as the reaction medium described above.

The reaction conditions for the preparation of methyl dithiocarbazinate can be as follows. The pH range of the reaction mixture can be about 8 to 14 and preferably 14 to 9, at a temperature of about 0° to 35° C. and preferably 5° to 25° C., for about 0.5 to 3 hours and preferably 1 to 2 hours. The reaction can be conducted without isolating the dithiocarbazinate salts. It is also a distinct feature of the invention that the methylating reaction can be conducted without the use of expensive reaction catalysts such as sodium iodide. In accordance with this invention, the methylating reaction consists essentially of reacting the reaction product containing the dithiocarbazinate with methyl bromide.

The resulting product containing methyl dithiocarbazinate can be isolated by any convenient means. Illustratively, methyl dithiocarbazinate can be isolated as a wet cake by filtering or centrifuging. The wet cake can be collected on a vacuum filter and washed with water to remove impurities such as bromide salts. The resulting cake can be used as such cake or dried by any convenient means. Illustratively, the cake can be dried by exposing to temperatures that would effect drying without causing decomposition. More specifically, the cake can be dried in a vacuum oven, using a nitrogen sparge at a temperature of about 30° to 40° C. Generally, the methyl dithiocarbazinate purity can be up to about 95% with variation attributable to washing and/or drying steps.

As would be realized from the foregoing, methyl dithiocarbazinate can be obtained without recrystalization of the reaction product containing the same. It is, therefore, a distinct feature of the invention that methyl dithiocarbazinate can be prepared without separating the intermediate dithiocarbazinate from the reaction medium. As such, the invention encompasses a process for preparing methyl dithiocarbazinate consisting essentially of reacting carbon disulfide and hydrazine in a non-alcoholic solvent, followed by methylating the hydrazinium dithiocarbazinate.

By the process of the invention, one obtains high yields of methyl dithiocarbazinate in high purity without the associated negative of dithiocarbazinate build-up on the surface of the reaction vessel and with a significantly more concentrated slurry than previously practical on an industrial scale. The elimination of the buildup of solids on the reaction vessel wall solved several problems. The reaction temperature can be more closely controlled due to improved heat transfer through the reaction vessel wall. Secondly, the reduction of available dithiocarbazinate increases the local methyl bromide concentration beyond desired limits resulting in increased by-product formation and subsequent lower yield and purity. Also by this process, one can eliminate the use of undesirable solvents such as ethanol and methylating agents such as methyl iodide. The process requires no isolation of intermediate dithiocarbazinate. The advantages of this invention with particular respect to yield and purity and the ability to transfer the product slurry for further processing on an industrial scale are clear when comparing the examples described below.

These and other aspects of the invention are further illustrated but are not intended to be limited by the following examples in which all parts and percentages are by weight unless otherwise specified.

EXAMPLES

Example 1

Carbon disulfide (38 g, 0.5 mole) was slowly added (with cooling) to a mixture of toluene (30 mL—i.e., about 0.3 moles), water (72 mL, 4 moles) and hydrazine monohydrate (50 g, 1.0 moles) at 25° C. The molar ratio of solvent to carbon disulfide was about 0.6:1. After the completion of the adds, the reaction was stirred for 1 hour, then methyl bromide gas (52.3 g, 0.55 moles) was bubbled in the mixture over 2 hours. The resulting white slurry was stirred for an additional 30 minutes at 25° C. then cooled to 5° C. and filtered any time during the batch. The batch was very fluid and easy to transfer from the reactor. Mixing of the batch was easy to perform. Methyl dithiocarbazinate (yield 87%, purity 98%) was isolated as a white powder.

Example 2 (Comparative)

A batch was made using the above procedure but with no toluene present. The batch had large quantities of solids deposited on the vessel wall during the carbon disulfide addition. The batch had a very high viscosity which made mixing difficult. The batch could not be poured out of the reactor and had to be scooped out by hand. Yield was 79% and purity was 87%.

Example 3 (Comparative)

A batch was made using the above procedure but with 15 mL of toluene (i.e., about 0.15 moles) present. The molar ratio of solvent to carbon disulfide was about 0.3:1. The batch had large quantities of solids deposited on the vessel wall during the carbon disulfide addition but not as many as comparative Example 2. The batch had a high viscosity which made mixing difficult. Yield was 81% and purity was 88%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In a process for the manufacture of methyl dithiocarbazinate comprising reacting carbon disulfide and hydrazine to form hydrazinium dithiocarbazinate and methylating said hydrazinium dithiocarbazinate with methyl bromide; the improvement wherein the reaction of said carbon disulfide and hydrazine is conducted in the presence of a non-alcoholic solvent to reduce dithiocarbazinate buildup, the molar ratio of said solvent to carbon disulfide being from about 0.4:1 to about 3:1.

2. The process according to claim 1 wherein said solvent is an aromatic or aliphatic hydrocarbon.

3. The process of claim 2 wherein said solvent is toluene.

4. The process of claim 1, wherein said molar ratio is from about 0.5:1 to about 3:1.

5. The process of claim 1 wherein the methylating reaction is followed by isolating methyl dithiocarbazinate as a wet cake by filtering or centrifuging.

6. The process of claim 1 wherein said reaction is also conducted in the presence of water, the molar ratio of water to carbon disulfide being from about 2:1 to about 10:1.

* * * * *